(12) United States Patent
Brun Del Re et al.

(10) Patent No.: US 6,807,438 B1
(45) Date of Patent: Oct. 19, 2004

(54) ELECTRIC FIELD SENSOR

(76) Inventors: Riccardo Brun Del Re, 1105 Grenon Avenue, Ottawa, Ontario (CA), K2B 1A9; Izmail Batkin, 911G - Ellsmere Road, Gloucester, Ontario (CA), K1J 8G4; Wayne Young, 2331 Cotters Cres., Gloucester, Ontario (CA), K1V 8Y7

( * ) Notice: Subject to any disclaimer, the term of this patent is extended or adjusted under 35 U.S.C. 154(b) by 0 days.

(21) Appl. No.: 10/049,675

(22) PCT Filed: Aug. 25, 2000

(86) PCT No.: PCT/CA00/00981

§ 371 (c)(1),
(2), (4) Date: Sep. 30, 2002

(87) PCT Pub. No.: WO01/16607

PCT Pub. Date: Mar. 8, 2001

(30) Foreign Application Priority Data

Aug. 26, 1999 (CA) .............................................. 2280996
Feb. 17, 2000 (US) ......................................... 09/505,732

(51) Int. Cl.[7] .................................................. A61B 5/04
(52) U.S. Cl. ........................ 600/372; 600/395; 600/523; 128/902
(58) Field of Search ............................... 600/372, 395, 600/523; 128/902

(56) References Cited

U.S. PATENT DOCUMENTS

| | | | |
|---|---|---|---|
| 3,500,823 A | * 3/1970 | Richardson et al. | ........ 600/372 |
| 3,568,662 A | * 3/1971 | Everett et al. | .............. 600/384 |
| 3,580,243 A | * 5/1971 | Johnson | ...................... 600/508 |
| 3,744,482 A | * 7/1973 | Kaufman et al. | ........... 600/372 |
| 3,880,146 A | * 4/1975 | Everett et al. | .............. 600/523 |
| 3,882,846 A | * 5/1975 | Fletcher et al. | ............. 600/395 |
| 4,296,754 A | * 10/1981 | Hennig et al. | .............. 600/507 |
| 4,602,639 A | * 7/1986 | Hoogendoorn et al. | ..... 600/372 |

OTHER PUBLICATIONS

Chippingdale et al, Review of Science & Instruments vol. 65(1) Jan. 1994, pp. 269–270.

* cited by examiner

Primary Examiner—Lee S. Cohen
(74) Attorney, Agent, or Firm—David J. French

(57) ABSTRACT

An electric field sensor employs a capacitive pick-up electrode in a voltage divider network connected to a body emanating an electric field. The system is relatively insensitive to variations in the separation gap between electrode and body, reducing sensor motion artifacts in the output signal and stabilizing its low frequency response. The pick-up electrode may be positioned at a "stand off" location, spaced from intimate contact with the surface of the body. This is equivalent to providing low level capacitive values for the capacitive coupling between the pick-up electrode and the body whose electric field is to be monitored. Or a series limiting capacitor may be provided in the input stage. Human body-generated electrical signals may be acquired without use of conductive gels and suction-based electrodes, without direct electrical contact to the body, and even through thin layers of clothing.

19 Claims, 11 Drawing Sheets

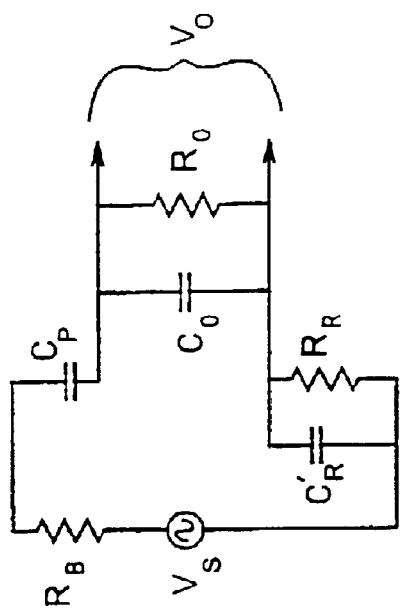
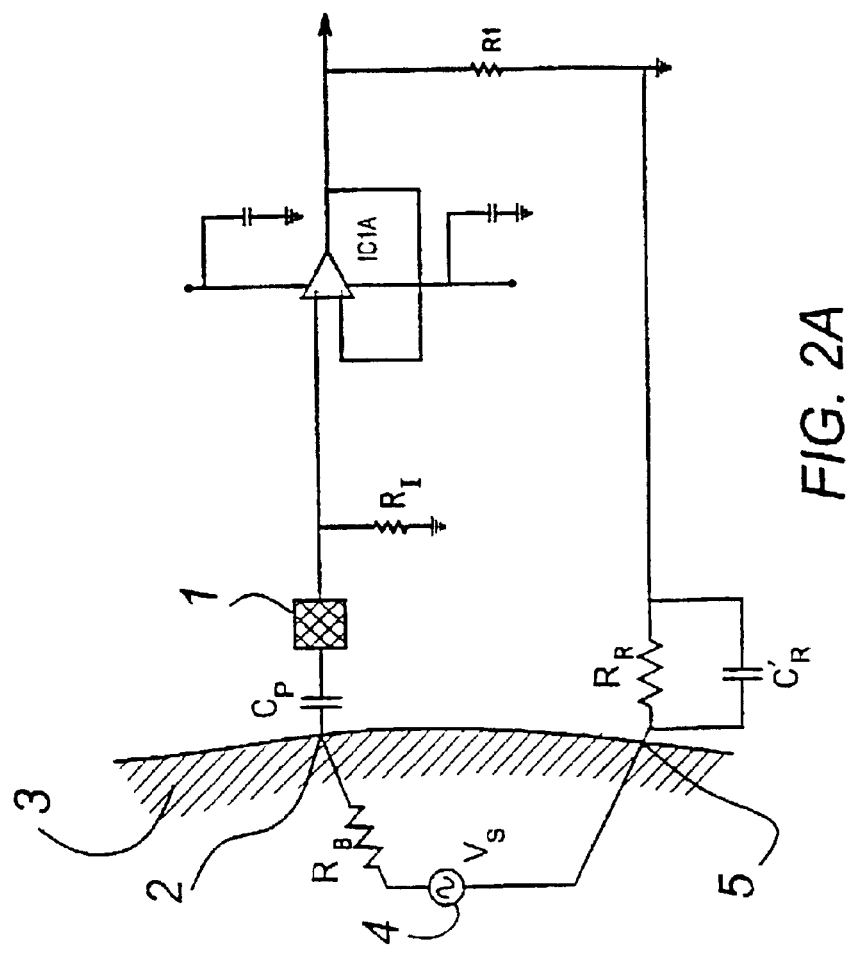
*FIG. 2B*
*FIG. 2A*

ELECTRIC FIELD SENSOR

FIELD OF THE INVENTION

This invention relates to electric field sensors in the medical field for the detection of alternating electrical fields originating from within the body to produce electro-cardiograms (ECGs) and electro-encephalograms (EEGs) and the like, as well as heart rate monitoring. It also relates to other applications for sensing external electric fields.

BACKGROUND TO THE INVENTION

The detection of electrical potentials occurring on the human body is the basis for ECG/EEG diagnostic procedures used to assess heart conditions and brain functions (hereafter "ECG"). An extensive science has been established on the basis of coupling conductive electrodes to the human body to sense the low-level electrical signals that the body is able to generate.

A feature of this technology in the past has been to focus on reducing electrical resistance at the skin/electrode interface. For this purpose ECG electrodes are often used in conjunction with conductive gels and suction cup attachment mechanisms. These arrangements are uncomfortable for the user, restrict mobility, and have limited useful life.
Dry Electrodes—Prior Art Approach Investigations have been made into using capacitive pick-ups to detect electrostatic potentials on the skin of a patient. Examples in the literature include the text "Introduction to Bio-Electrodes" by Clifford D. Ferris, published by Plenum Press in 1974. In this text the author discusses experiments with insulated, capacitive electrodes based upon the configuration (page 184):

"Body surface (skin)/Dielectric/metal/FET".

A shielded single electrode and a two-electrode circuit based on a capacitive electrode are depicted on page 185. Electrode capacitance is reported as 14 uF/cm$^2$ at page 187.

The text "Electrodes and Measurement of Bio-Electric Events" by L. A. Geddes, published in 1972 by Wiley-Interscience discusses "dry electrodes" at pages 98–103. A single electrode circuit based on a insulated anodized electrode and FET transistor is depicted at page 100. A value for electrode capacitance is reported at page 102 as being 3200 picoFarads Capacitance ranges of 5000–20000 picoFarads/cm$^2$ are referenced at page 102. In particular, this reference reports (page 102):

"At present there are attempts to provide ultra thin films of insulating materials having high dielectric constants and strengths so that a high electrode-to-subject capacitance will be attained . . . ".

This statement recites that obtaining a high level of capacitive coupling is an objective and necessarily presumes that such electrodes will be placed in intimate contact with the body of the subject being measured.

In the text "Principles of Applied Biomedical Instrumentation" 2nd edition, L. A. Geddes, L. E. Bater published by Wiley Interscience, 1975, the author observes (at page 217):

"To obtain an electrode-subject impedance that is as low as possible, every effort is made to obtain a high capacitance by using a very thin dielectric having a high dielectric constant."

Capacitance values from 5,000 pF/cm$^2$ to 20,000 pF/cm$^2$ are cited.

A Technical Note entitled "New Technologies for In-Flight, Pasteless Bioelectrodes" by D. Prutchi and A. M. Sagi-Dolev, published in Aviation, Space and Environmental Medicine, June 1993 (page 552) describes a capacitive, dry bioelectrode for obtaining EEG and ECG signals obtained through a plate anodized with aluminum oxide. Coating thicknesses of 50 um and 170 um are referenced. Allowing for a dielectric value of 10 (for aluminum oxide) this thickness would provide an electrode with the ability to develop a capacitance of about 50 pF/cm$^2$ to 180 pF/cm$^2$, if intimately presented to a conducting surface.

Accordingly, the prior art has addressed the problem of capacitive dry electrodes in terms of developing high capacitive values for insulated electrodes placed in intimate contact with the surface being monitored. These prior investigative efforts have been focused on maximizing the coupling between the electrode and the skin surface carrying the potential to be detected. This has led to electrodes that employ thin dielectric surfaces that are capable of providing capacitive values from about 50–1000 picoFarads/cm$^2$ and higher. It is a necessary adjunct to establishing high capacitive coupling to a body that the electrodes be pressed intimately against the surface being sensed, and that the surface be smooth and free of defects.
True Effective Capacitance It is believed that all of the capacitive values cited in the prior art references are based on the premise that cited capacitance values are for the maximum capacitance that an insulated electrode can develop when pressed against a conductive surface.

A capacitive pickup electrode for an ECG system may be designed to have a capacitive value of several hundred picoFarads per square centimeters when its insulated plate surface is laid over a smooth, highly conductive counter-electrode surface, such as a sheet of copper. This is the condition for maximum capacitance. However, when placed proximate to the human skin, the dead layer of the skin acts effectively as an insulating spacer, removing the plate of the pickup electrode further from the source of the electric field being sensed. In such a configuration, the effective value of the capacitive coupling between a typical, high capacitance pickup electrode e.g. 100$^+$ pF/cm$^2$ and the field source within the human body may be on the order of 1–100 picoFarads/cm$^2$ depending on the intimacy of contact with the body and the presence of sweat or hair on the skin. The prior art has endeavoured to maximize this capacitance value.
Difficulties of Intimate Coupling The results of prior art endeavours have been only moderately successful. One problem that has arisen is the extensive sensitivity of these capacitive electrodes of prior design to variations in the gap or intimacy of contact between the electrode and the skin. When intimate contact is the objective, even the presence of hair or sweat can cause variations in the value of capacitive coupling being established. The procedure of pressing dry electrodes against the body has presented similar inconveniences to those arising in the use of conductive electrodes, e.g., discomfort and limited mobility due to intimate contact protocols. In particular, prior art systems have never been reported as operating through clothing fabric. No proposal has been made to obtain alternating electrical signals of the ECG, EEG type, etc. through use of dry capacitive electrodes that are not positioned at fixed locations on the skin surface of a subject.

Further difficulties associated with the use of dry electrodes pressed into intimate contact with the skin of a person are tribo-electric effects—electrical charges created by sliding friction and pressure. Tribo-electric effects deliver large, essentially static charges, to the pickup electrode.

Such charges impose a near DC or very low frequency drift in the background level over which the more relevant, higher frequency signals are imposed. To discharge the amplifier input and pickup electrode of such capacitively acquired charge, the input resistive impedance of the high impedance first stage amplifier should be carefully selected.

Thus a particular concern when sensing alternating signals is the band-pass capabilities of the sensing system. Ideally, the pickup electrode should drive an amplifier with a complementary input impedance which, in the case of ECGs is able to process low level, e.g. milli-volt, signals in the range 0.05 $H_z$ to 150 $H_z$. The lower cut-off frequency should be stable in order to restore the bias value of the driven amplifiers to its normal value in cases where the circuit is over-driven by a very low frequency or DC offset signal.

To minimize the disruptions caused by very low frequency or DC over-driven off-sets, the capacitive coupling to the body (C) should be matched to the input impedance of the amplifier sensor (R) via a preferred, tuned RC-relation. This allows the sensor to have a stable band pass. U.S. Pat. No. 3,744,482 addresses this issue with a tuned feed-back loop. However, for the tuning of the sensor input to be consistent, both the resistive –R and capacitive –C values should be stable.

Variance in Capacitance

A pickup electrode may be of such a design as to permit it to achieve high value capacitive coupling, as for example maximum values of 50–100+ picoFarads/$cm^2$ when placed on a conductive plate. This can be effected through use of thin or high dielectric value insulative layers. A difficulty arises, however, in ensuring that the frequency cut-off of the RC network at the input stage is appropriately tuned when the pickup electrode is capable of high capacitance coupling. This difficulty arises from the fact that a pickup electrode with potentially high capacitance will exhibit varying actual capacitive coupling values when placed adjacent to the body generating the electric field, particularly when an attempt is made to place such an electrode in intimate contact with the skin of the human body being sensed.

By example, the actual capacitive coupling value may range over several hundred percent if the electrode is pressed very tightly against skin wetted with body sweat. In this situation, since capacitance varies inversely with the gap separating with the capacitor electrodes, the system is operating in the separation-sensitive region of a graphic plot of capacitance vs Separation Distance (of FIG. 5).

When the effective capacitance of the pickup electrode varies substantially, the cut-off value of the RC filter arrangement will vary correspondingly. This will reduce the performance of the RC combination as a well-tuned, high-pass, low frequency cut-off filter. Settling times for low frequency signal artifacts will be lengthened as the capacitive value of C is doubled or tripled.

Background Noise Rejection

A major source of noise for electronic systems is ambient 60 Hz signals (in North America) arising from the power system. It is known that sixty hertz background noise can be eliminated or greatly reduced through the use of a differential amplifier arrangement. However, for maximum rejection of common mode noise to be achieved, the inputs to both branches of the differential amplifier should be fully balanced. If the inputs are not balanced improper signal differencing will occur and the output will be disturbed by the imbalance. In the case of ECG systems, balance would ideally be achieved by having two separate ECG pickup electrodes couple to the source body originating the electrical field with the same degree of capacitive coupling.

Where intimate-contact, high capacitance electrodes are employed, this balancing is hard to maintain. A need exists for a more stable system to be employed for these types of applications. The invention herein addresses this need.

In summary, a need exists in the medical field to provide an electrical field sensor for detecting alternating signals that is less demanding in terms of electrode/body coupling. In non-medical fields, useful applications may also arise where the measurement of an oscillating surface charge is to be effected without contact arising between the charged surface and the electrical sensor. The invention herein addresses such needs.

The invention in its general form will first be described, and then its implementation in terms of specific embodiments will be detailed with reference to the drawings following hereafter. These embodiments are intended to demonstrate the principle of the invention, and the manner of its implementation. The invention in its broadest and more specific forms will then be further described, and defined, in each of the individual claims which conclude this Specification.

SUMMARY OF THE INVENTION

According to one aspect of the invention the signal pickup procedure for obtaining an electric field or ECG signal and the like is carried-out under a configuration wherein the effective capacitance coupling the electrical field source to a high impedance sensing amplifier is relatively insensitive to variations in the separation between the body that serves as a field source and the pickup electrode. Small displacements of the pick-up electrode lead to little change in the degree of capacitance coupling between the electrical field source and the sensing amplifier.

According to the invention in one aspect, an electric field sensor is provided that includes a first pickup electrode for placement next to a surface whose electrical field is to be sensed through capacitive coupling. This pickup electrode is not operated, as in the past, to achieve high capacitive coupling values for such electrodes, i.e. operating in the separation-sensitive region of a Capacitance vs. Separation Distance graph (as per FIG. 5). Rather, by the arrangements of the present invention, the value of the capacitive couplings between the source field and the sensing amplifier is kept small i.e. under 40 picoFarads/$cm^2$, preferably 20 picoFarads/$cm^2$, more preferably, 1–10 picoFarads/$cm^2$. This may be achieved by avoiding intimate contact with the body e.g. by positioning the plate of the pickup electrode at a "stand-off" location that reduces the sensitivity of the measured output to motion effects i.e. variations in the separation of the pick-up electrode from the surface of the body being sensed. And it may be achieved by placing a limiting capacitor in series with the input to the sensing amplifier.

To ensure the "stand-off" effect of the invention first arrangement is achieved, an insulating layer may be provided over the electrode to separate it from a body by a gap that ensures that capacitive coupling does not vary sensitivity with separation. In some cases, useful signals can be obtained by placing sensors of the invention over protective layers already present on the body.

The objective in designing the sensor in accordance with this criterion is to ensure that the overall, effective capacitance formed between the pick-up electrode and any surface that may be presented to the outer face of the pick-up electrode will always have a value in the region of a plot of capacitance value versus separation distance wherein, upon displacement of the electrode by a standard amount, the capacitance is varied by a limited percentage value.

Equivalently, changes in the surface condition of the field-emitting object, e.g. the appearance of sweat on skin, does not significantly change the degree of capacitive coupling that is present when the sensor is operating under the conditions of the invention.

In particular, and preferably, when the separation of the electrode from the surface varies by 0.1 mm or less, the capacitance value of the coupling between the body and the pick-up electrode varies by less than 50%. More preferably the capacitive value varies by less than 20%.

By providing an ECG pickup with an insulative layer that precludes the pickup electrode from achieving capacitance values of higher than a specific value, e.g. 40, 20 or less, preferably 10 picoFarads/cm$^2$, an ECG system so equipped will be inherently suited for operation in the preferred, second, separation-insensitive region (as per FIG. 5). The presence of such a capacitance-limiting insulative layer will preclude an electrode from operating in the first, separation sensitive zone.

It is preferable for the insulating layer to have a thickness which is equal to, or greater than, the size of surface irregularities of the body being measured, and equal to or greater than the variations in the sensor-to-body separation gap.

This is completely counter-intuitive to the methodologies applied by the prior art experiments with capacitive, "dry" electrodes which employ extremely thin dielectric layers and then proceed to place the sensor in intimate contact with the surface of the body being sensed.

Thus, the present invention, in one aspect, employs a dielectric layer for the pick-up electrode that ensures that sensing is occurring at a stand-off location which is insensitive to minor motion and/or surface irregularities as well as temporal changes in surface characteristics.

The instability arising from the variations in the coupling capacitance of the pickup electrode can be addressed in a further manner, namely by inserting into the input of the high impedance sensing amplifier that receives signals from the pickup electrode a series capacitor of fixed and limited value. This limiting capacitor should preferably have a minimum value that is greater than the input capacitance of the amplifier stage that is driven by the signal received from the body through both the pickup electrode and the limiting capacitor. As a preferred upper limit, the limiting capacitor may have a value that is less than the effective coupling capacitance between the pickup electrode and the body. Values for this limiting capacitor outside this preferred range may also be adopted. The inclusion of such a series capacitor has the same effect in constraining variations in the effective, overall capacitance value of the coupling between the electrical field source and the input amplifier as the "stan-doff" variant of the invention referenced above.

When this alternate procedure for rendering the input amplifier relatively insensitive to the electrode/body separation distance, e.g. placing a limiting capacitor in series at the input to the first stage amplifier, is employed, use of a series limiting capacitor of appropriate value, e.g. 40 picoFarads, will set an upper limit on the capacitance coupling between the field source and the input amplifier. As the pickup electrode is in series with the limiting capacitor, the combined capacitance of the two cannot exceed the value of the limiting capacitance. Because the value of the limiting capacitor is fixed, the RC value for the high pass filter at the input stage is stabilized. Even if the pickup electrode has a relatively high maximum possible capacitance, e.g. over 1000 picoFarads, because it is in series with the limiting capacitor, it cannot absorb a substantial static charge. Viewed alternately, if the pickup electrode were to achieve in fact, a very high level of capacitance coupling to the body, at a value greatly exceeding the capacitance value of the limiting capacitor e.g. 10:1, then we may treat it as having a minimal, or transparent impedance contribution to the combined series capacitance of the amplifier's input. This will still leave the limiting capacitor, e.g. 40 pf as dominating the capacitive coupling between the field source and the input amplifier.

Voltage Divider Network

In detecting electric field signals through the capacitive pickup arrangement of the invention, the signal being sensed by the input amplifier is essentially being taken from across a voltage divider network defined by the pickup electrode, the limiting capacitor (if present), the input capacitance of the amplifier and the remaining electrical coupling (either resistive or capacitive or both) at the other end of the voltage divider network which is connected to the body which is the source of the electric field. Assuming this last connection is of relatively low impedance, the signal strength seen at the input to the amplifier depends on the ratio of the input capacitance of the amplifier to the other capacitors in the series chain. If the input capacitance of the amplifier is small, then most of the signal strength will appear across this capacitance, and be sensed by the amplifier.

In actual use, the effective capacitive value of the pickup electrode may be on the order of the value of the limiting capacitor. In this case, its impedance contribution will become significant. For example, the pickup electrode effective coupling capacitance being equal in value to that of the limiting capacitance—e.g. 40 picoFarads—then the combined, net capacitance of these two elements in series would drop to half of their individual capacitance values e.g. 20 picoFarads. This will not, however, have a serious deleterious effect on the signal detection performance of the overall system so long as the input capacitance to the high impedance amplifier is small e.g. 2–5 picoFarads.

Differential Amplifier/Dual Inputs

As is done in the case of conductive electrode ECG systems, two pick-up sensors may be applied at two distinct locations on the skin. By taking the difference in the output signals from two locations on the body the benefits of common mode noise rejection may be obtained. The objective of minimizing variations in such capacitance values is also important for this special case arrangement in ECG-measuring systems: the use of dual input differential amplifiers to obtain rejection of common mode noise.

Differential amplifiers used to reject common mode noise, e.g. ambient 60 Hz, fail to achieve full rejection when the bias levels of the amplifiers are imbalanced or if the amplifiers have unequal RC characteristics. To maximize the prospects that these levels and characteristics are balanced, both branches of the pickup elements should have similar settling times when disrupted by an off-setting, very low frequency signal. This requires that the effective capacitance of the couplings within both branches between the sensed body and amplifier inputs be similar. The invention addresses means for achieving this last criterion.

Clothing-Supported Arrays

On the foregoing basis, this invention provides a means for detecting electrical fields present on the surface of a body without the use of conductive gels and suction-based appliances. Useful signals may be obtained based on the combination of multiple electrodes assembled in a fixed, preformated array. Thus, multiple electrodes, e.g. 4 or more, may be carried by a clothing-type of support as an array that can be readily donned or removed with minimal inconvenience. This provides considerable freedom for the tele-monitoring of patients while they engage in daily routines. Freedom from the limitations of conventional tele-monitoring arrangements represents a valuable advance in this field.

The foregoing summarizes the principal features of the invention and some of its optional aspects. The invention may be further understood by the description of the preferred embodiments, in conjunction with the drawings, which now follow.

BRIEF DESCRIPTION OF THE DRAWINGS

FIG. 2A is FIG. 1A with the substitution of a resistive, conductive coupling to the body at one end of the voltage divider network. A smaller parallel capacitive coupling remains present as well.

FIG. 2B is a conventional electrical schematic corresponding to FIG. 2A.

DESCRIPTION OF THE PREFERRED EMBODIMENT

Figure 1B:
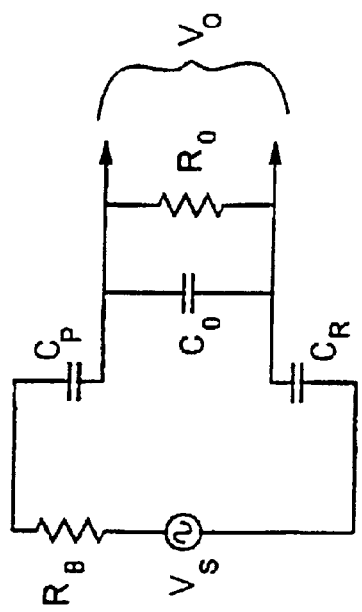
FIG. 1B is a conventional electrical schematic corresponding to the input portion driving the amplifier of FIG. 1A.
Figure 1A:
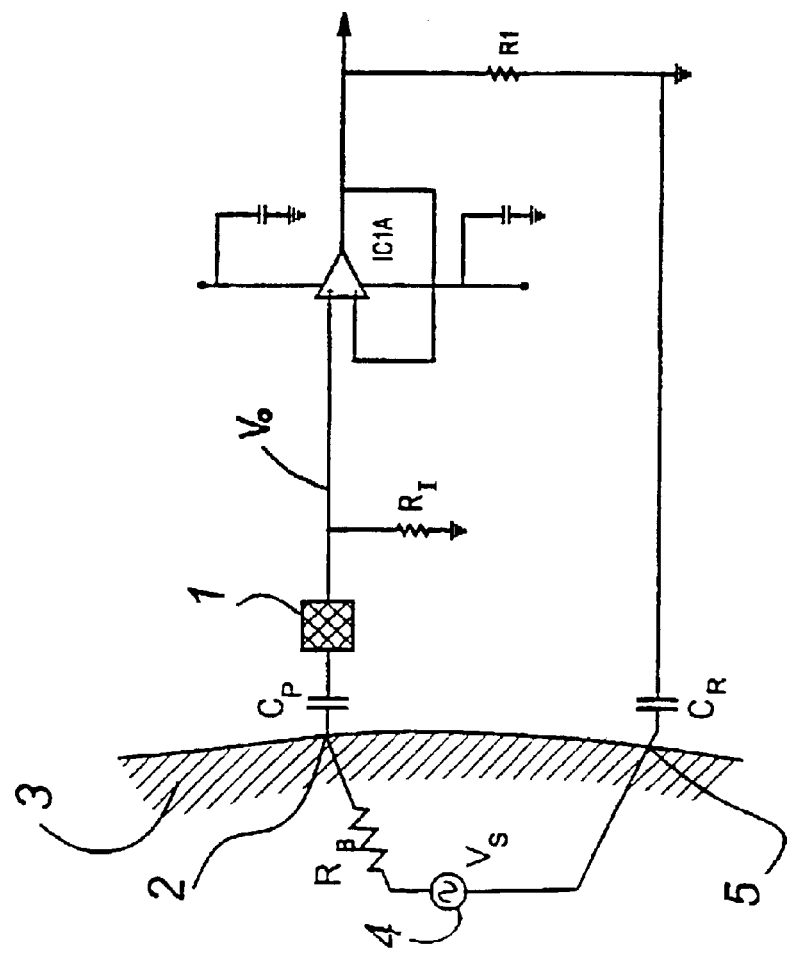
FIG. 1A is a combined pictorial/electrical schematic depiction of a single pick-up of the invention in position adjacent to a body whose electrical field is to be sensed. The voltage divider network is capacitively coupled to the body at both ends and drives an operational amplifier.

In FIG. 1A a pictorial schematic is shown of an electrical sensor system incorporating a pick-up electrode 1 in the form of a flat conductive surface placed adjacent a first location 2 on a body 3 where an electrical signal is to be sensed originating from an electrical signal generator 4 within the body 3 that provides a source voltage $V_B$. The pick-up electrode 1 develops a capacitive coupling to the body 3 through an intervening dielectric layer separating it from the body 3. This capacitive coupling for the pick-up electrode 1 is represented schematically by the capacitor $C_R$ The electrode 1 is connected to the input of an operational amplifier—IC1A, or its equivalent such as a field effect transistor. Input resistance $R_I$ connected between the amplifier input and circuit ground has a resistance value of on the order of $10^{12}$ ohms and serves to discharge the input of DC offsets and restore proper voltage input levels while accepting signals of the desired frequency.

The output $V_O$ from the voltage divider network which drives the operational amplifier IC1A, shown in FIG. 1B, is measured across input resistor $R_I$ that extends between the input of the operational amplifier IC1A through circuit ground to a reference capacitor $C_R$ that is coupled to the body 3 at a second, separate location 5. This location 5 may be separated from the first location 2 in obtaining conventional ECG signals. The locations 2,5 may also be proximate, e.g. adjacent, at certain body locations and still provide useful signals.

Capacitive coupling through reference capacitor $C_R$ is effected by means of an electrode (not shown in FIG. 1A) that is separated from the body 3 by a non-conducting material that acts as a dielectric. Conveniently, the case for an on-board battery holder can serve as this electrode, as shown further below.

The "standoff" or low-capacitance feature of the invention enables signal pickup without skin shaving and over some clothing layers. As a natural outcome of standoff operation, electrodes of the invention are less sensitive to the electrode dielectric characteristics than those of the prior art. Satisfactory values of electrode dielectric constants have been found in the range 1 to 10 and the signal characteristics on unprepared skin, hairy skin, and over clothing are essentially unchanged over this range. Flexible and compressible materials with advantageous mechanical properties can now be used.

These advantages arise because the nominal electrode capacitance in "standoff" operation is less than the typical "parasitic" capacitance which is created between the body and the electrode (see section "True Effective Capacitance"). The parasitic capacitance is an unavoidable consequence of hair, air, dead skin layers, skin inhomogeneities, and clothing fabrics. The standoff dielectric restricts the electrode capacitance to values which are smaller, and thus dominant, over the parasitic capacitance. This is essentially the reverse of the condition found in prior art electrodes where parasitic effects could dominate the coupling on hairy skin and where over-clothing pickup was not feasible for similar reasons.

This aspect of the invention enables the use of electrode materials not suitable for prior art capacitive electrodes and possessing highly desirable mechanical properties. Materials such as rubbers, plastics, foams, and fabrics can be used as electrode substrates in order to provide flexibility, elasticity, softness and conformability to the body. These features provide advantages of user comfort and mechanical stability of the electrode when placed against the body. Furthermore a wide range of materials can be used for the internal construction of electrodes providing flexibility, compressibility etc to the whole electrode structure. This is in contrast to prior art which required stiff constructions to provide mechanical support for brittle, fragile, or moderately flexible, thin substrates possessing carefully contrived dielectric and mechanical properties.

Inside the body 3, the signal generator 4 is seen as being subject to internal resistance $R_B$ within the body 3.

The input portion of circuit of FIG. 1A is redrawn as FIG. 1B in more conventional form. In FIG. 1B, the capacitance $C_O$ arises from the combined input capacitance of the operational amplifier IC1A and the input resistor $R_I$. The total apparent input resistance of this amplifier is represented by $R_O$, including the resistive value of the input resistor $R_I$. Collectively, the capacitances $C_P$, $C_O$, $C_R$ act as a voltage divider network whereby the output voltage $V_O$ is proportional to the source voltage $V_S$.

In FIGS. 2A and 2B, the coupling to the body 3 at the end of the voltage divider network opposite to the pick-up electrode 1, is effected principally by a direct, conductive contact. The resistance of the interface is indicated by $R_R$. Necessarily, some slight capacitance coupling is also still present, indicated by $C'_R$.

The output signal of the sensor is extracted by measuring the voltage difference across an electrical component in the voltage divider network that is connected to the subject electrical source. This should be done through a high impedance, low capacitance sensing circuit or sensing means to minimize signal loss. A field effect transistor or operational amplifier having an input impedance of on the order of $10^{12}$ ohms and an input capacitance of about 3 picoFarads has been found to be satisfactory when the other capacitor(s) in the voltage divider network have values of on the order of 10 picoFarads. Used in conjunction with a pickup electrode having an area of on the order of one to ten square centimetres, dielectric media having a total effective dielectric constant of 1–10 and a body-to-surface gap distance of on the order of 0.1 to 4 millimetres, signal values of the order of 1 millivolt or less may be detected from the skin surface of the human body.

With this type of sensor configuration useful signals may be obtained with the plate of the pick-up electrode separated from the skin or sensed body by a gap that allows the pick-up to qualify as a "stand-off" electrode. As the gap varies, the strength of the output signal will vary. But by operating the sensor in the capacitance/gap separation region specified by the criterion of the invention, such variations will not detract inordinately from the value of the signals being obtained.

Figure 5:
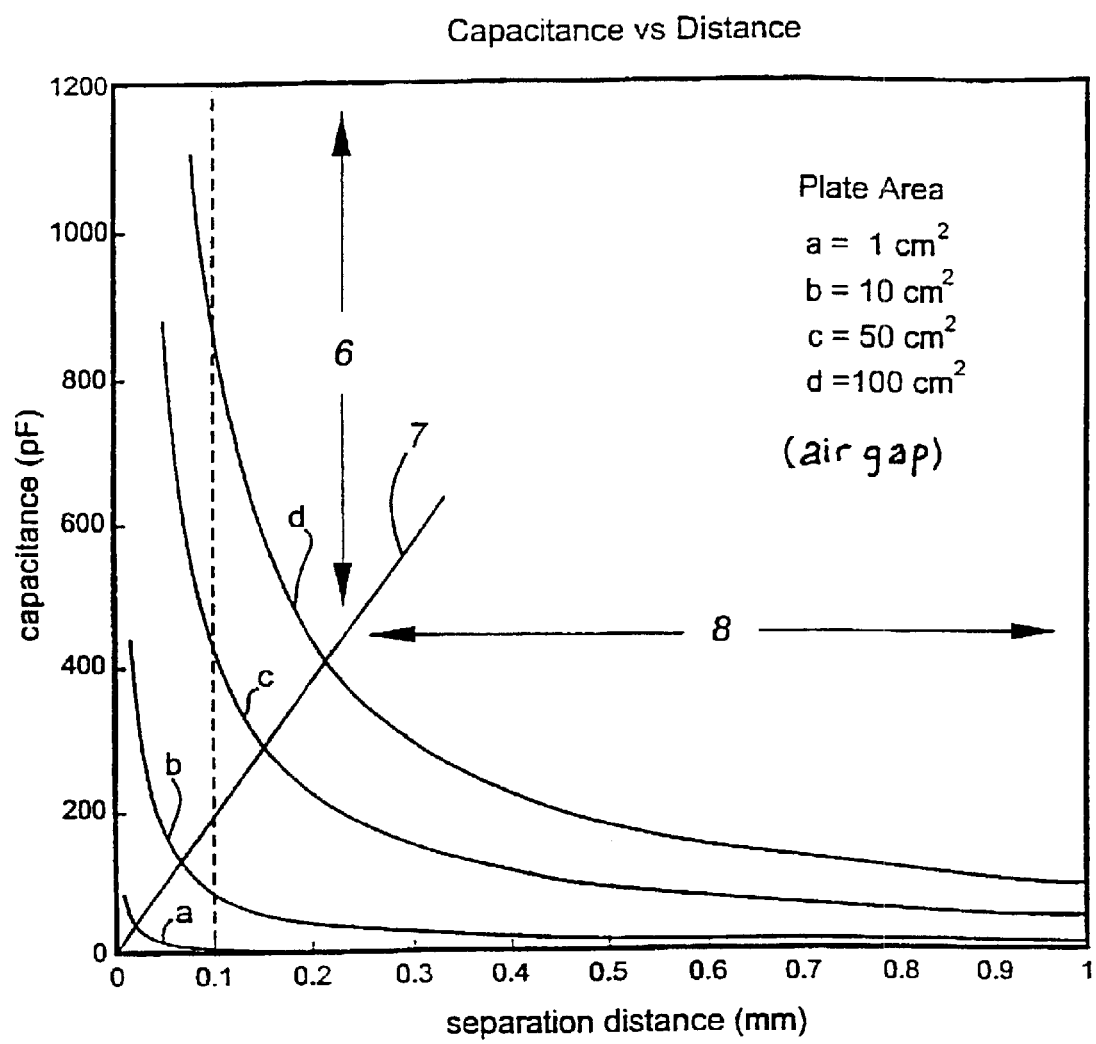
FIG. 5 is a graph showing the change of capacitance of pick-up electrodes with various surface areas as a function of separation distance for the electrodes.

A pickup electrode that is removed (i.e. placed at a distance) somewhat from the electrical field source is able to supply a satisfactory signal by reason of the mathematical relationship that exists between the value of capacitance and the separation distance existing between capacitor plates or electrodes, of FIG. 5. Since capacitance varies inversely with separation, the mathematical form of a curve for capacitance value plotted against separation distance is in the shape of a hyperbola. This means that the capacitance performance of a pickup electrode can operate in two distinct regions:

1) a first region wherein the separation distance is small and the curve is steep, corresponding to the situation where the capacitance value will vary highly, with great sensitivity, in response to small changes in the separation distance; and
2) a second region wherein the separation is greater, the curve is relatively flat, and the capacitance value varies relatively insensitively with similar changes in the separation distance. For the purposes of the present invention, the preferred region of operation according to one variant of the invention is in the second, separation-insensitive zone.

In FIG. 5 a graphic plot is depicted of the variation of capacitance C with a variation in the separation distance d at various separation distances d, based upon the theoretical formula:

$$C = k \cdot A / d$$

where: C is the effective capacitance of, for example $C_P$,
d is the separation distance of the electrode plate from the body giving rise to the capacitance,
A is the area, or effective area, of the pick-up electrode 1; and
k is a proportionality constant affected by the dielectric material in the separation gap.

In FIG. 5 the value of the dielectric constant is assumed to be that of air, i.e. 1.0 and the plates forming the capacitance are assumed to be fully conductive. This is therefore an idealized variant on the case of coupling to the human body.

Four curves are shown in FIG. 5 for pick-up electrodes 1 having surface areas as follows:
a=1 cm²
b=10 cm²
c=50 cm²
d=100 cm²

Each capacitance curve can be separated into two important regions: region 6, in which the capacitance changes relatively rapidly with a given change in separation distance; and region 8 of the invention in which the capacitance changes relatively slowly with a similar given change in separation distance. These regions are generally separated on FIG. 5 by boundary line 7.

For a capacitor with an electrode area of 1 cm², the line 7 passes approximately through a capacitive value of about 40 picoFarads. For capacitors with an electrode area of around 25 cm² the line 7 passes approximately through a capacitive value (of about 200 picofarads. For capacitive values above 200 picoFarads, region 6 approximately corresponds to the zone with d=0.1 mm or less; while for capacitive values below 200 picofarads region 8 approximately corresponds to the values above d=0.1 mm.

An important implication of FIG. 5 is that sensors with capacitance values within region 6 are very sensitive to small additional changes in the separation distance (delta-d). In contrast, sensors with capacitance values corresponding to region 8 are relatively insensitive to such changes. This is illustrated more succinctly in FIG. 6.

Figure 6:
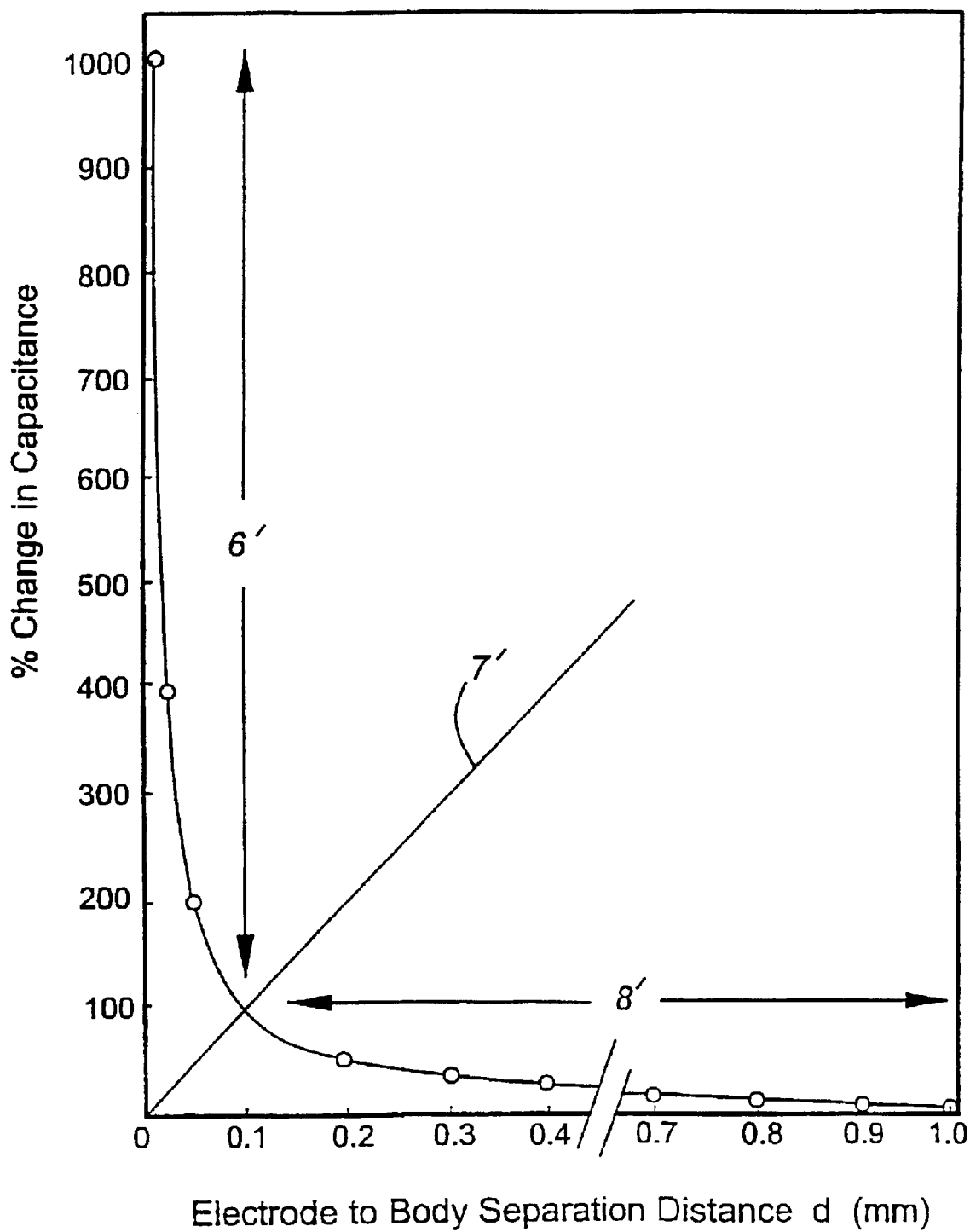
FIG. 6 is a graph showing the percentage change in capacitance for a 0.1 mm change in electrode-to-body gap distance as a function of nominal electrode-to-body gap distance over a range of 0.0 to 1.0 mm, assuming the body acts as a perfect electrode.

In FIG. 6, the percentage change in capacitance 15 corresponding to a delta-d=0.1 mm is graphed as a function of the nominal separation distance d.

FIG. 6 is dimensionless along the Y axis and applies to all capacitive sensors which obey or approximately obey the relation C=kA/d. According to the invention the capacitive value of the pick-up electrode, and other capacitive sensors when employed, are designed to operate in region 8' of FIG. 6, as opposed to region 6' from which it is separated by boundary line 7'.

In the region 8' this latter regime the capacitance, and hence the output signal is sufficiently insensitive to spatial and temporal body surface variations so as to provide the advantages of signal stability inherent in the invention.

Figure 10:
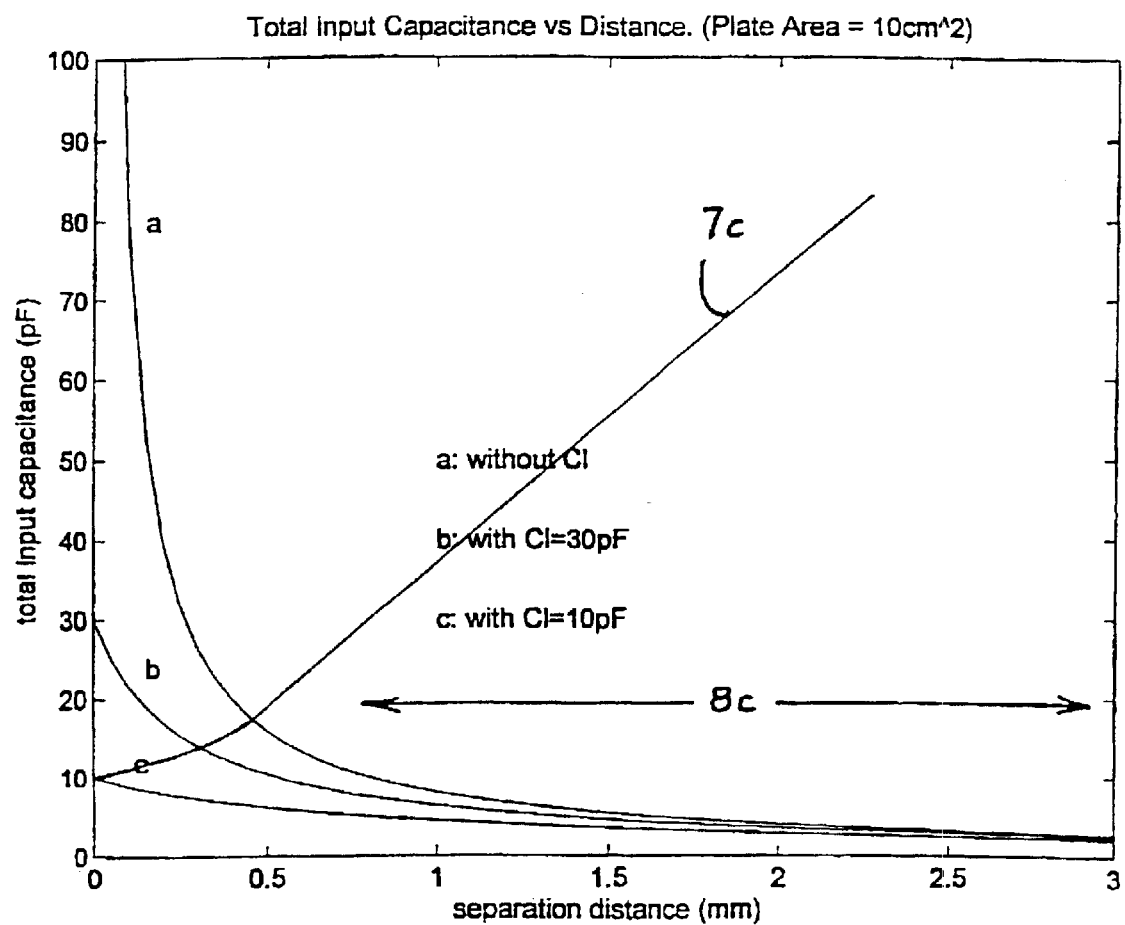
FIG. 10 is a graph of total effective coupling capacitance between the sensed body and the input to the amplifier of the sensor, plotted as a function of the separation distance of the electrode from the surface being sensed. Three curves are shown, two with a limiting series capacitor present and one with no limiting capacitor present.
Figure 11:
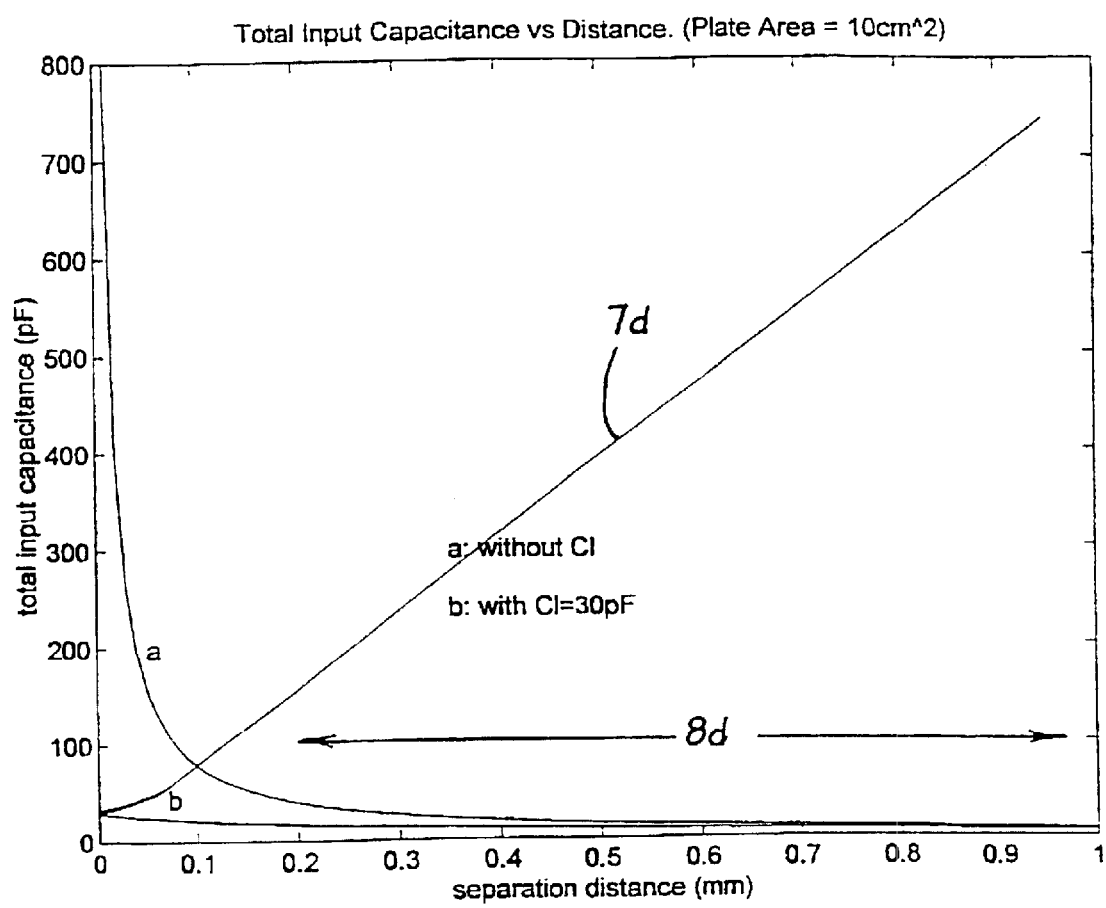
FIG. 11 is similar to FIG. 10 but with the vertical scale for the input capacitance increased by a factor of ten and showing one curve with and one curve without a limiting capacitor present.

FIGS. 5 and 6 premise that operation in regions 8 and 8' can be effected by achieving low capacitance coupling between the body and the pickup electrode. FIGS. 10 and 11 apply to an alternate case wherein the capacitive coupling between the pickup electrode and the body is high, but the results of achieving system operation in preferred regions 8,8' is still obtained. This is achieved by insertion of a series limiting capacitor $C_L$ in the input to the first stage amplifier of the sensor.

This series limiting capacitor may have a preferred value that is greater than the input capacitance of the first stage amplifier, and less than the effective value of the capacitance coupling between the pickup electrode and the body whose electrical field is being sensed, e.g. between 5 and 40 picoFarads.

Figure 1D:
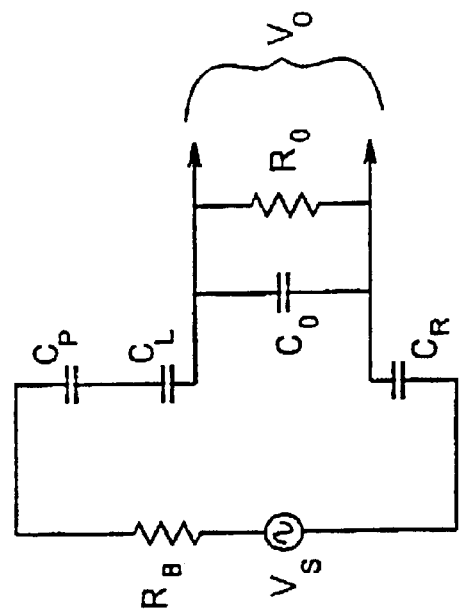
FIGS. 1C and 1D are the schematics of FIG. 1A and 1B with the added presence of a series capacitor in the amplifier input.
Figure 1C:
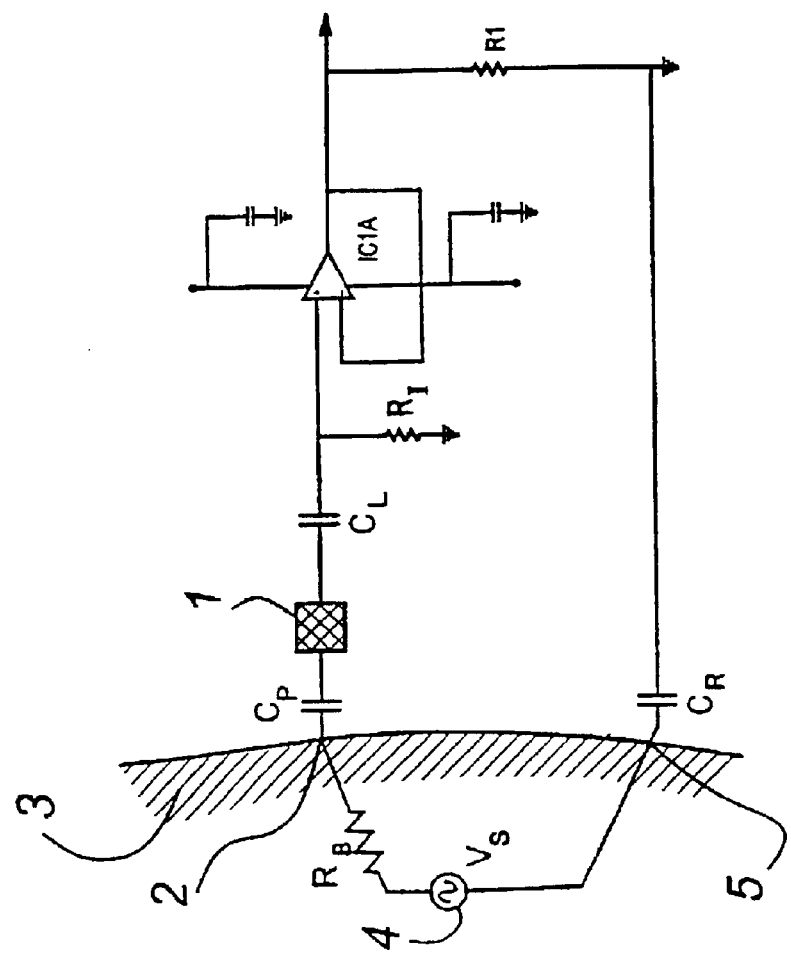

In FIGS. 1A and 1B the pickup capacitor $C_P$ is shown as being directly coupled to the operational amplifier 1C1A. In FIGS. 1C and 1D a series capacitor $C_L$ is shown added between the pickup capacitor $C_P$ and the amplifier input (at which $V_O$ is detected). The effect of this limiting capacitor $C_L$ is to place a maximum value on the capacitance extending between the body 3 and the signal sensing means 1C1A. The pickup electrode's capacitance $C_P$ is in series with the limiting capacitor $C_L$. Collectively, they behave as a single capacitor having a total net value $C_T = 1/(1/C_L + 1/C_P)$.

FIGS. 10 and 11 plot the behaviour of $C_T$ as a function of the separation distance present for the pickup capacitor $C_P$.

This net value capacitor $C_T$ provides a more stable, separation-insensitive circuit performance that occurs in its absence. This is particularly true when $C_L$ is smaller than $C_P$.

A convenient formula for establishing a value for $C_L$ is that $C_L$ should be less than 5 (picoFarads/cm$^2$) times the area of the pickup electrode (in cm$^2$).

The consequence is that a similar regions 8c, 8d of insensitivity to displacement of the pickup electrode exists in FIGS. 10 and 11, parallelling regions 8 and 8' in FIGS. 5 and 6 and delimited by line 7c, 7d. A similar preferred criterion for performance of the invention can also be established for the circuit arrangement of FIG. 1C, 1D, namely, a 0.1 mm displacement of the pickup electrode causes a 50% or small change in the net capacitance Cn. Preferably the change is less than 20% more preferably, less than 10%.

Thus, the same effect of desensitizing the signal pickup and coupling capacitance from DC offsets can be achieved through the presence of a limiting capacitor $C_L$ in the input link between the pickup capacitor $C_P$ and the signal sensing means 1C1A.

Over-Driven Amplifier

For the present invention, the input resistance present at the input to the high impedance amplifier can be provided from two sources:

1) the inherent input resistance of the amplifier, typically $10^{13}$–$10^{14}$ ohms;

2) the input resistance of an added, external, input resistor, $R_I$.

A preferred value for this resistance $R_I$ may be determined by considering the pickup electrode and input resistance as an RC high frequency passing filter.

Assuming an effective pickup electrode capacitive value of 60 picoFarads and a low frequency cut-off of 0.05 Hz established by the RC input value of the first stage amplifier, a preferred value of $4 \times 10^{12}$ ohms may be provided for the input stage input resistance $R_I$.

Occasionally, the near-DC signals delivered to the pickup electrode will be so substantial as to drive the signal at the input amplifier to the limit of its range of response. When overdriven, the recovery period (before a normal input level can be re-established by the input resistor) is increased. To shorten the recovery period in such cases it is convenient to provide the input stage with a non-linear input resistance.

Figure 3:
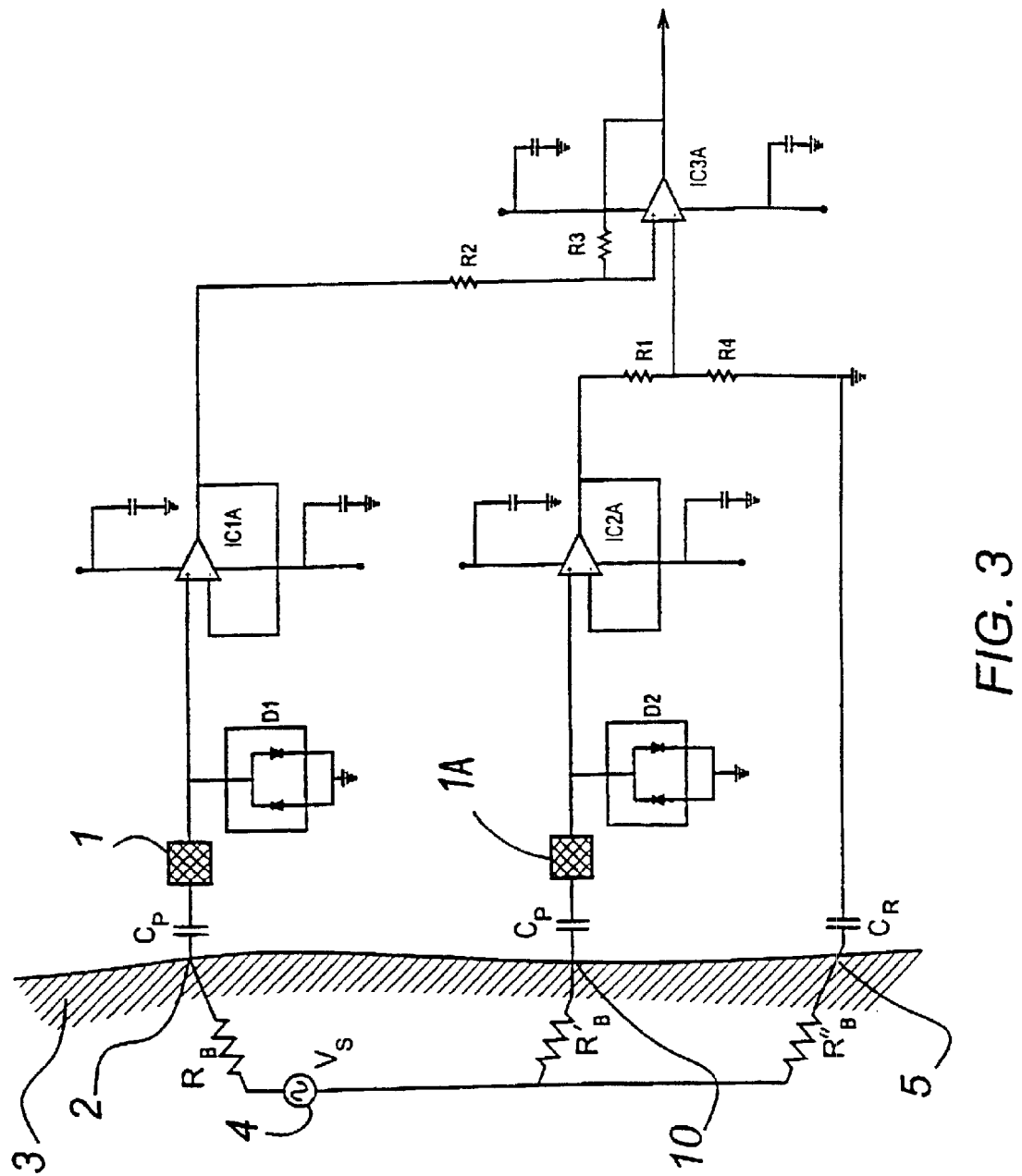
FIG. 3 is an electrical schematic for a dual pickup electrode configuration, based on the pick-up of FIG. 1A, with signals being fed to a differential amplifier, but with dual, parallel Schotkey diodes as input leakage resistors.

This can be achieved by grounding the input through pairs of Schotkey diodes, $D_1$, $D_2$ in FIG. 3, connected in parallel.

The forward resistance of Schotkey diodes before breakdown occurs can be on the order of $10^{13}$ ohms. By choosing diodes with a forward breakdown voltage that is above the level of the signal of interest, the "reset" function of the input resistance of the high impedance amplifier can be improved. If the breakdown voltage of the Schotkey diode is chosen to be at the voltage level for saturation of the input amplifier, then the "shorting" effect occurring after breakdown will not distort the signal of interest as long as the amplifier is operating within or inside its saturation cut-off limits.

As the forward resistance of the Schotkey diodes prior to breakdown may be higher than the appropriate value to provide an input resistance suited to the given low frequency cut-off for the RC filter, such diodes $D_1$, $D_2$ may have to be accompanied by a parallel input resistor $R_I$ that establishes the appropriate net value for input resistance for small level signals.

In FIG. 3 two pick-ups similar to that of FIG. 1A (except for the substitution of diodes $D_1$, $D_2$ for the input resistor $R_I$) are used to drive a differential amplifier IC3A through input operational amplifiers IC1A and IC2A. The second additional pickup electrode 1A is placed at a location 10, separated from the first and second locations 2 and 5. Within the body the signal source $V_S$ may be treated as distributing its potential over the resistors $R_B/R'_B/R_B$.

By use of this differential signal detection circuit, common mode noise present in the two pick-up circuits will be minimized.

Figure 4:
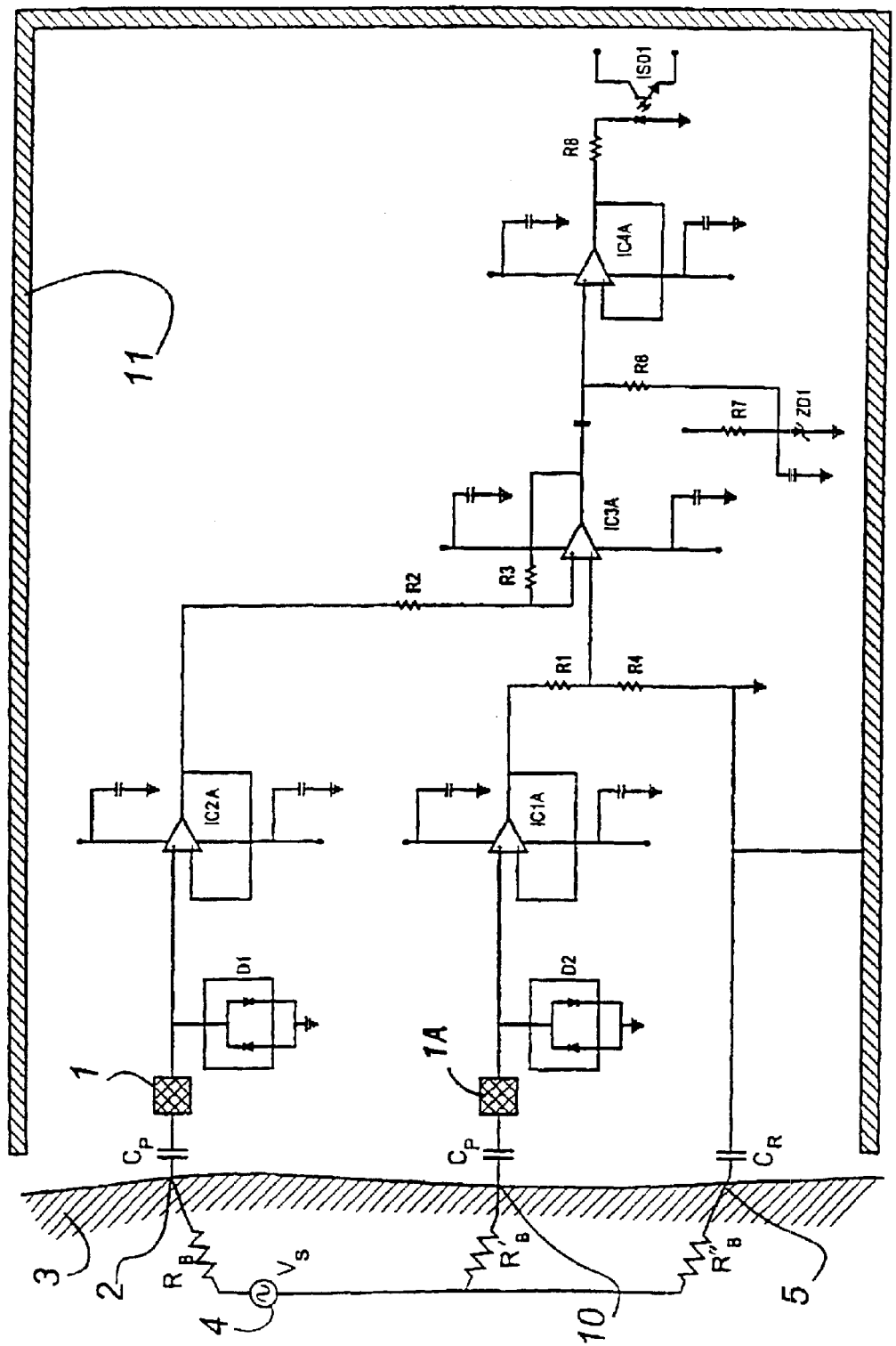
FIG. 4 is an expanded electrical schematic of the circuit of FIG. 3 with the additional presence of an amplifier and optical coupler to provide electrical isolation.

FIG. 4 shows the circuit of FIG. 3 extended by an optical isolator IS01 driven by an operational amplifier IC4A which is, in turn, driven by the output from the differential amplifier 1C3A. By mounting these circuits as close as possible to the pick-up electrode 1 1A, interference from ambient 60 Hz electromagnetic signals can be minimized.

In FIG. 4, a shielding conductive layer 11 is depicted as overlying the externally-directed side of the circuitry. This layer/structure 11 is preferably connected to the circuit common point but need not necessarily be so connected. In some configurations this shield may be "floating". Its role is to exclude effects arising from intruding electromagnetic signals, e.g. 60 Hz, originating in the environment. In non-earthed applications the shield distributes ambient, intruding signals equally to both pickups, contributing to common mode noise rejection. It is highly desirable that a shield of some type be employed in one or other of such configurations.

Figure 7:
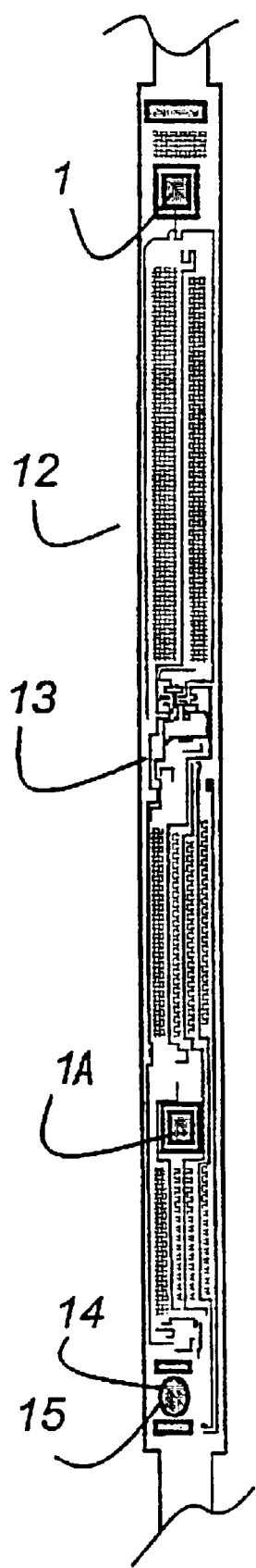
FIG. 7 is a plan view of an electrical circuit corresponding to FIG. 4 laid-out in a belt to be worn over the chest of a patient.

In FIG. 7 a belt 12 is depicted that carries the circuit of FIG. 4. The hatched areas are decorative. The pick-up electrodes 1, 1A are mounted on a substrate 13 comprising a MYLAR™ or KAPTON™ film that serves both as a spacer and as an insulating dielectric of approximately 0.13 mm thickness. The pick-up electrodes 1, 1A have been measured against a copper plate as providing a capacitance value of 20 picoFarads respectively.

The pickup electrodes are completed by the addition of a "standoff" dielectric which is bonded to the undersurface of the Mylar or Kapton film directly beneath the electrodes. Had the original film been chosen of sufficient thickness to realize the full benefits of "standoff" operation, the extra dielectric would be optional.

The belt 12 of FIG. 7 has its own on-board power supply in the form of batteries 14. The case 15 of the batteries 14 is connected to circuit common point and serves as an electrode to provide the reference capacitor $C_R$. A measured value for its capacitance, when placed against a copper plate, of 160 picoFarads has been observed with the case 15 coupled to the entire circuit. The substrate 13 for the belt 12, is made of KAPTON™ has a thickness of 5 thousandths of an inch. This forms the principal dielectric element for $C_R$. The nature of the dielectric material has little effect on the invention for reasons discussed above.

The shield 11 (not shown but present) in the belt 12 of FIG. 7 is in the form of a flexible conductive layer, with an insulated undersurface that overlies the circuitry on the outer side portion of the belt 12. This shielding layer should be close enough to the pickup electrodes 1 to evenly distribute ambient noise signals, and sufficiently spaced from the pickup electrode/body interface so as to not detract from signal pickup by the pickup electrodes.

Figure 8:
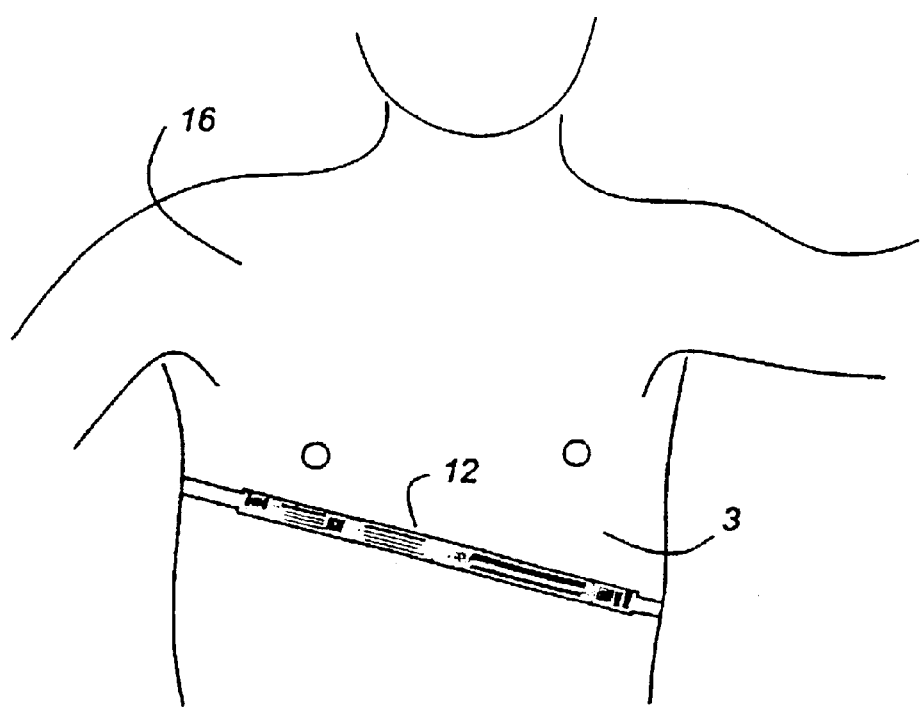
FIG. 8 is a pictorial depiction of the belt of FIG. 7 in place over the chest of a patient.

The pick-up electrodes 1, 1A in FIG. 4 are held by the substrate 13 of the belt 12, at a fixed interval. This interval is dimensioned to permit the electrodes 1 to respectively overlie electrical nodes (not shown) on the body 3 of a wearer 16 as shown in FIG. 8. The belt 12 is held in place by tension developed by connectors, e.g. hook-and-loop fastening means, once positioned on the body 3. While a narrow belt 12 is depicted in FIG. 8, a wider belt or vest 15 could carry three, four or more electrodes 1 as shown in FIG. 9.

An advantage of the invention is that multiple pickup electrodes can be assembled in a preformated, fixed array that can be fitted to the body collectively, as a unitary assembly, much as in the manner of donning an article of clothing. This permits a wearer to be "fitted-up" for electrical field measurement in a very short period of time. Data acquisition can readily be suspended and resumed by the simple act of removing and then re-donning the pre-assembled array. No components are consumed in this process.

Figure 9:
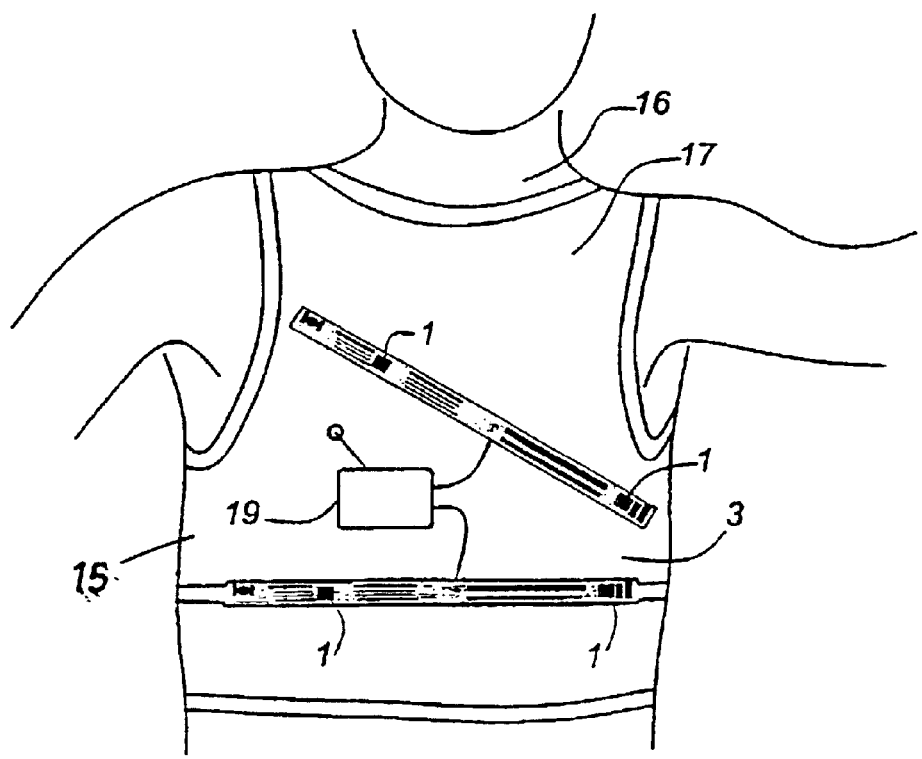
FIG. 9 is a pictorial version of a garment worn by a patient that carries four pick-up electrodes.

The electrodes 1 of such a piece of apparel as shown in FIG. 9 may feed signals to a radio transmitter 19 carried by the wearer 16. In this manner an especially convenient form of tele-monitoring can be achieved.

Apart from the option of providing the pickup electrode with an insulative layer that inherently suits its operation in the preferred, separation-insensitive zone, the actual freedom from having to place the pickup electrode in intimate contact with the body whose field is to be sensed, has considerable advantages. These include:

1) the pickup electrode need not be tightly fixed at a specific location on the skin. Small lateral displacements are permissible. Adhesives are avoided;

2) the pickup electrode need not be applied under excessive pressure against the skin. Discomfort is avoided;

3) the skin need not be prepared to receive the electrode, as by shaving or rubbing;

4) an insulative layer, such as a pad or layer of clothing may be present between the electrode and the skin. This can be useful to increase comfort and absorb sweat. With the electrode at a removed, "stand-off", location, the presence of sweat on the skin does not substantially affect the degree of capacitive coupling between the body and the amplifier; and 5) Conformable or compressible electrode substrates such as foams and fabrics can be used for comfort and mechanical stability. This is unlike the prior art which utilized hard dielectric surfaces or thin films of limited flexibility that required mechanically stiff constructions and were incapable of fitting around all body curvatures.

These are substantial conveniences for patients who must submit to ECG examinations. This is particularly true in respect to extended-period ECG monitoring procedures.

CONCLUSION

The foregoing has constituted a description of specific embodiments showing how the invention may be applied and put into use. These embodiments are only exemplary. The invention in its broadest, and more specific aspects, is further described and defined in the claims which now follow.

These claims, and the language used therein, are to be understood in terms of the variants of the invention which have been described. They are not to be restricted to such variants, but are to be read as covering the full scope of the invention as is implicit within the invention and the disclosure that has been provided herein.

What is claimed is:

1. An electric potential sensor for detecting an electrical potential difference present over a source surface comprising:

(1) a voltage divider network including at one end a pick-up electrode with a face surface having an insulating layer positioned adjacent to said face surface for placement next to a source surface whose electrical field is to be sensed through capacitive coupling (2) an electrical coupling at the other end of the voltage divider network for connection to another portion of the source surface over which an electrical potential difference exists; and (3) voltage sensing means for providing a voltage output, said voltage sensing means having an input capacitance that forms a portion of the voltage divider network, the voltage sensing means being connected for measuring the voltage appearing across that portion of the voltage divider network provided by said input capacitance and for providing a voltage output that corresponds to the strength of said electrical potential difference characterized in that the capacitance that can exist between the source surface and the voltage sensing means is sufficient so that, when the pickup electrode is placed adjacent the source surface, the change in the capacitive coupling between the voltage sensing means and the source surface arising from a change in the separation distance between the pickup electrode and said surface varies insensitively with displacement of the electrode towards or away from the surface whereby, upon variation of the separation distance between the source surface and the pick-up electrode, the overall, effective capacitance formed in use between said source surface and the voltage sensing means through the pick-up electrode is such that the change in capacitance is leas than 50 percent when subjected to a 0.1 mm increase in said separation distance, and wherein the voltage sensing means has an input resistance that, when combined with the capacitance that can exist between the source surface and the voltage sensing means through the pick-up electrode, provides an RC filter with a low-frequency cut-off of at least 0.05 hertz.

2. A sensor as in claim 1 wherein the voltage output of the voltage sensing means is an unmodulated voltage output that corresponds to the strength of said electrical potential difference.

3. A sensor as in claim 1 wherein the percentage change in capacitance is less than 20% when a 0.1 mm increase in the separation distance occurs.

4. A sensor as in claim 1 wherein said insulating layer is of such dimensions as to preclude the electrode from providing a capacitance value of over 40 picoFarads/cm$^2$.

5. A sensor as in claim 1 wherein said insulating layer is of such dimensions as to preclude the electrode from providing a capacitance value of over 20 picoFarads/cm$^2$.

6. A sensor as in claim 1 wherein said insulating layer is of such dimensions as to preclude the electrode from providing a capacitance value of over 10 picoFarads/cm$^2$.

7. A sensor as in claim 1 comprising a series capacitor, positioned within said voltage divider network between said pickup electrode and the voltage sensing means, said series capacitor having a value in picoFarads of less than five times the area of the pick-up electrode in cm$^2$.

8. A sensor as in claim 7 wherein said series capacitor has a value of between 5 and 40 picoFarads.

9. A sensor as in claim 1 comprising a leakage resistor in parallel with the input capacitance of the voltage sensing means of between $10^{11}$ and $10^{13}$ ohms.

10. A sensor as in claim 1 comprising a capacitive coupling for connection to the source surface at the end of the voltage divider network opposite the pick-up electrode.

11. A sensor as in claim 1 comprising a resistive-contact coupling for connection to the source surface at the end of the voltage divider network opposite the pick-up electrode, said resistive contact coupling having a resistance value of 500 k ohms, or less.

12. A sensor assembly system comprising a first sensor as in claim 1 and a second sensor as in claim 1 applied at a spaced separation over the source surface, said first and second sensors being connected to a differential amplifier to obtain the difference in the output signals from two locations on the surface with common mode noise rejection.

13. A sensor assembly comprising multiple sensors each as in claim 1 assembled on a carrier to locate the pick-up electrodes of each sensor in a fixed, preformated array.

14. A sensor assembly as in claim 13 wherein the carrier is a piece of clothing that can be readily donned or removed with minimal inconvenience.

15. A sensor assembly as in claim 13 combined with tele-monitoring means.

16. A method of sensing an electrical potential difference present over a surface comprising:
   (1) presenting a pickup electrode to confront said surface and to establish a capacitive coupling to said surface and receive a signal based upon the electric field emanating therefrom;
   (2) applying the signal so received to a voltage divider network which includes at one end the pick-up electrode and at another end an electrical coupling means connected to another portion of the surface over which an electrical potential difference exists, there being a high impedance amplifier with an input capacitance connected in series within said voltage divider network, the high impedance amplifier having an input resistance that, when combined with the capacitance that can exist between said surface and the high impedance amplifier through the pick-up electrode, provides an RC filter with a low-frequency cut-off of at least 0.05 hertz;
   (3) maintaining the pickup electrode at a spaced separation from the confronted, field-emanating surface so that the overall effective capacitance between said surface and said amplifier has a value in the region of a plot of capacitance value versus separation distance wherein the percentage change in capacitance is no greater than 50 percent when subjected to a 0.1 mm increase in the separation distance occurring between the pick-up electrode and the confronted surface
whereby a signal is provided to the amplifier to provide an amplifier output voltage that corresponds to the strength of said electrical potential difference, and wherein the capacitive coupling between the field-emanating surface and the amplifier through the pickup electrode varies insensitively with displacement of the electrode away from said surface.

17. A method as in claim 16 wherein the percentage change in the capacitance is less than 20% when a 0.1 mm increase in the separation distance occurs.

18. A method as in claim 16 wherein the pickup electrode has a surface confronting face that is provided with an insulative dielectric layer having a thickness such as to preclude the electrode from providing a capacitance value of over 40 picoFarads per centimeter squared.

19. A method as in claim 16 wherein the voltage divider network includes a series limiting capacitor between the pickup electrode and the input to the amplifier, the pickup electrode having a value of between 5 and 40 picoFarads.

* * * * *

UNITED STATES PATENT AND TRADEMARK OFFICE
CERTIFICATE OF CORRECTION

PATENT NO.   : 6,807,438 B1
DATED        : October 19, 2004
INVENTOR(S)  : Riccardo Brun Del Re, Izmail Batkin and Wayne Young It is certified that error appears in the above-identified patent and that said Letters Patent is hereby corrected as shown below:

<u>Column 8,</u>
Line 17, after the words "FIG. 1B," insert -- an unmodulated output, --

Signed and Sealed this

Fifth Day of April, 2005

JON W. DUDAS
*Director of the United States Patent and Trademark Office*